(12) United States Patent
Bradley

(10) Patent No.: US 12,317,940 B2
(45) Date of Patent: Jun. 3, 2025

(54) BLOOD FLOW RESTRICTION SPORTSWEAR GARMENT

(71) Applicant: HYTRO LIMITED, West Byfleet (GB)

(72) Inventor: Warren Bradley, Liverpool (GB)

(73) Assignee: HYTRO LIMITED (GB)

(*) Notice: Subject to any disclaimer, the term of this patent is extended or adjusted under 35 U.S.C. 154(b) by 316 days.

(21) Appl. No.: 16/972,907

(22) PCT Filed: May 31, 2019

(86) PCT No.: PCT/GB2019/051515
§ 371 (c)(1),
(2) Date: Dec. 7, 2020

(87) PCT Pub. No.: WO2019/239107
PCT Pub. Date: Dec. 19, 2019

(65) Prior Publication Data
US 2021/0244106 A1    Aug. 12, 2021

(30) Foreign Application Priority Data
Jun. 14, 2018   (GB) .................................. 1809772.5

(51) Int. Cl.
*A41D 13/00*     (2006.01)
*A41D 31/18*     (2019.01)
*A63B 69/00*     (2006.01)

(52) U.S. Cl.
CPC ......... *A41D 13/0015* (2013.01); *A41D 31/18* (2019.02); *A63B 69/0057* (2013.01); *A41D 2300/22* (2013.01); *A41D 2400/32* (2013.01); *A41D 2600/10* (2013.01)

(58) Field of Classification Search
CPC ................ A41D 13/0015; A41D 31/18; A41D 2300/22; A41D 2400/32; A41D 2600/10; A63B 69/0057
USPC ............................................................. 2/69
See application file for complete search history.

(56) References Cited

U.S. PATENT DOCUMENTS

| | | | |
|---|---|---|---|
| 5,267,928 A | 12/1993 | Barile et al. | |
| 7,604,651 B1 | 10/2009 | Harris et al. | |
| 8,176,571 B2* | 5/2012 | Kato .......................... | A41F 9/02 2/237 |
| 9,144,253 B1 | 9/2015 | Munter et al. | |
| 2010/0037369 A1 | 2/2010 | Reichert | |

(Continued)

FOREIGN PATENT DOCUMENTS

| | | |
|---|---|---|
| CN | 200966713 Y | 10/2007 |
| JP | H10309328 | 11/1998 |

(Continued)

OTHER PUBLICATIONS

Sato Yoshiaki, Garment With Buckles, WO 2004062404 A1, Jul. 29, 2004 (Year: 2004).*

(Continued)

*Primary Examiner* — Sally Haden
(74) *Attorney, Agent, or Firm* — Garvey, Smith & Nehrbass, Patent Attorneys, L.L.C.; Seth M. Nehrbass; Fabian M. Nehrbass

(57) ABSTRACT

A sportswear garment comprising means for adjustably compressing at least one major vein in a user's limb such that blood flow through the at least one major vein is restricted.

17 Claims, 12 Drawing Sheets

(56) References Cited

U.S. PATENT DOCUMENTS

| | | | |
|---|---|---|---|
| 2013/0017933 A1* | 1/2013 | Foster | A41D 31/102 2/69 |
| 2015/0328033 A1 | 11/2015 | Ingimundarson et al. | |
| 2015/0359542 A1* | 12/2015 | Steinbaugh | A61B 17/1327 606/203 |
| 2016/0113339 A1 | 4/2016 | Dolcetti | |
| 2016/0262461 A1 | 9/2016 | Berns et al. | |
| 2017/0224357 A1 | 8/2017 | Whalen et al. | |
| 2017/0354422 A1 | 12/2017 | Brub | |

FOREIGN PATENT DOCUMENTS

| | | |
|---|---|---|
| JP | H10309328 A | 11/1998 |
| JP | 2001513379 | 9/2001 |
| JP | 2004218135 A | 8/2004 |
| JP | 2017522459 | 8/2017 |
| NO | 2018017632 A1 | 1/2018 |
| WO | WO9909850 | 3/1999 |
| WO | WO2004062404 | 7/2004 |
| WO | WO2015200672 | 12/2015 |
| WO | 2018/013188 A1 | 1/2018 |

OTHER PUBLICATIONS

Horii ,Tourniquet Belt, (JP H10309328 A);Dec. 17, 2015 (Year: 2015).*

Examination report, App. No. 202047054334, Intellectual Property India, Government of India, Jul. 13, 2022, 5 pages.

The Third Office Action, Application No. 2019800370762, Chinese Patent Office, Jun. 2, 2022, 8 pages.

1 Office Action, Chinese Patent Office, Aug. 31, 2021.

Pro X and Pro BFR Bands Comparison' product video, available at: https://www.youtube.com/watch?v=ZhoF-Vwrs-A, published on Oct. 20, 2017 [accessed on Nov. 22, 2018].

International Search Report, EPO, completed Sep. 5, 2019, mailed Sep. 18, 2019, International application No. PCT/GB2019/051515, 4 pages.

Written Opinion of the International Searching Authority, EPO, completed Sep. 5, 2019, International application No. PCT/GB2019/051515, 5 pages.

Search Report under Section 17(5), Application No. GB180772.5, Nov. 22, 2018, 4 pages.

* cited by examiner

BLOOD FLOW RESTRICTION SPORTSWEAR GARMENT

This invention relates to a garment incorporating blood flow restriction technology.

BACKGROUND

Blood flow restriction (BFR) training, also known as vascular occlusion training, is an exercise technique designed rapidly to increase muscle mass. A major vein, or major veins, proximate to the muscle being exercised is compressed such that blood flowing through the major vein is reduced. This impedes venous return at the muscle causing venous pooling and leading to metabolic stress. This may subsequently result in rapid muscle growth i.e. a faster building of muscle tissue in comparison to the same muscle stress exercises without impeding venous return. An existing BFR technique involves tying a strap around a desired limb. This existing technique has the disadvantage that each time the user wishes to incorporate BFR into their training, they must find the right position for the strap on the limb such that a pressure asserted by the strap is applied to the correct position where the major vein is located. It may be difficult correctly to position the strap on the desired muscle each time BFR is implemented in order correctly to apply pressure to the major vein and not, for example, an artery. The existing technique has the further disadvantage that the user must find the correct pressure to be exerted by the strap on the major vein for each use. It may be difficult to adjust the tension in the strap to apply the correct amount of pressure to compress the major vein by a desirable amount. A yet further disadvantage is that the strap can be unsightly. The user may wish to do some regular training without the strap, in which case the user may have to carry the strap or keep the strap in a pocket.

BRIEF SUMMARY OF THE DISCLOSURE

Viewed from one aspect, there is provided a sportswear garment comprising an adjustable compression member to compress at least one major vein in a user's limb such that blood flow through the at least one major vein is restricted while permitting blood flow through major arteries in the user's limb, wherein either:
  i) the garment is a top or t-shirt and the compression member is located in a sleeve of the top or t-shirt such that, in use, the compression member is positioned over an upper part of the user's arm proximate to the user's armpit; or
  ii) the garment is a pair of shorts or a pair of trousers and the compression member is located in the leg of the pair of shorts or pair of trousers such that, in use, the compression member is positioned over an upper part of the user's thigh proximate to the user's groin.

The garment is designed so that the compression member is correctly positioned to restrict blood flow in the at least one major vein in the user's upper arm or thigh without also unduly restricting arterial blood flow, which may lead to faster muscle growth in the upper arm or thigh in comparison to exercising when wearing regular sportswear garments.

The garment may comprise a sleeve or housing for housing the compression member to adjustably compress the at least one major vein. This may allow the compression member to be obscured or hidden, for example when the compression member is not being used to restrict blood flow, so that the garment appears to be a regular sportswear garment. It also ensures that the user has the option of using BFR any time they are wearing the garment. Separate BFR apparatus can be lost and may be inconvenient to carry around.

The sleeve or housing of the garment may be made of the same fabric as the rest of the garment. This may allow for a seamless look to the garment. It may also increase a durability of the garment as the compression member is repeatedly tugged and pulled by the user when adjusting.

The compression member may comprise an elastic strap configured to be adjustable between a first configuration in which the compression member does not compress the at least one major vein and a second configuration in which the elastic strap is under tension and compresses the at least one major vein. The tension in the elastic strap may lead to compression of the at least one major vein.

The elastic strap may have first and second ends, and at least one of the first and second ends may be moveable relative to the other of the first and second ends so as to adjust the elastic strap between the first and second configurations. This may ensure that the elastic strap remains in a state of tension for continual compression of the major vein when BFR is desired.

The first end of the elastic strap may be fixedly secured to the garment and the second end of the elastic strap may be configured to be releasably secured to the garment. This may allow the user repeatedly to switch the garment between a mode wherein BFR is implemented to a regular mode.

The second end of the elastic strap may be configured to at least partially protrude from the housing when the elastic strap is in the first configuration. This may allow the user easily to grip the elastic strap to move it from the first configuration to the second configuration.

The second end may be configured to be releasably secured to the garment by a hook and loop type fastening. In one embodiment, one of a strap of hooks or loops of the hook and loop type fastening may be attached to an exterior surface of the sleeve or housing and another of the strap of loops or hooks may be attached to an inside surface of the elastic strap proximate to the second end of the elastic strap. This may allow adequate adhesion of the elastic strap to the sleeve or housing. It also has the benefit that it is light and is without any inconvenient protrusions (i.e. is flat).

In some embodiments, at least one of the first and second ends is connected to a rotary dial with a ratchet mechanism, and rotation of the dial may allow the elastic strap to be tensioned. Suitable mechanisms of this type are disclosed, for example, in WO 99/09850 in relation to a footwear lacing system, the content of which is incorporated into the present application by reference.

The garment may further comprise indicia to indicate an amount of compression applied by the compression member to the at least one major vein. In some embodiments, the amount of compression is a function of the amount of tension in the elastic strap. By providing indicia, for example in the form of markings along at least one of a length of the elastic strap, the sleeve or housing, and/or the hook and loop fastening or around the rotary dial, it is possible for a user to make a note of where they found a comfortable, effective level of tension in the elastic strap, and easily to re-establish the same level of tension upon subsequent usage of the garment.

In some embodiments, the second end of the elastic strap may be configured to be detachably attached to the garment by a catch configured to be hooked though one of a plurality of eyelets incorporated into the sleeve or housing, wherein the catch may be attached to an inside surface of the elastic strap proximate to the second end of the elastic strap. This may allow secure releasable attachment of the elastic strap to the sleeve or housing. It may also have a better aesthetic than the loop and hook type fastening. Furthermore, the catch may be embossed with a logo of the sportswear garment.

In some embodiments, an underside of the elastic strap may be provided with a pad or protrusion configured to apply additional pressure on the user's limb at a position appropriate to restrict blood flow in at least one major vein but to allow blood flow in major arteries. The pad or protrusion may be substantially solid, or may in some embodiments be cushioned for comfort. A position of the pad or protrusion along the length of the elastic strap may in some embodiments be adjustable by a user so as to allow correct positioning. The pad or protrusion can be held in place with a clip or other securing device.

BRIEF DESCRIPTION OF THE DRAWINGS

Embodiments of the invention are further described hereinafter with reference to the accompanying drawings, in which.

DETAILED DESCRIPTION

Figure 1:
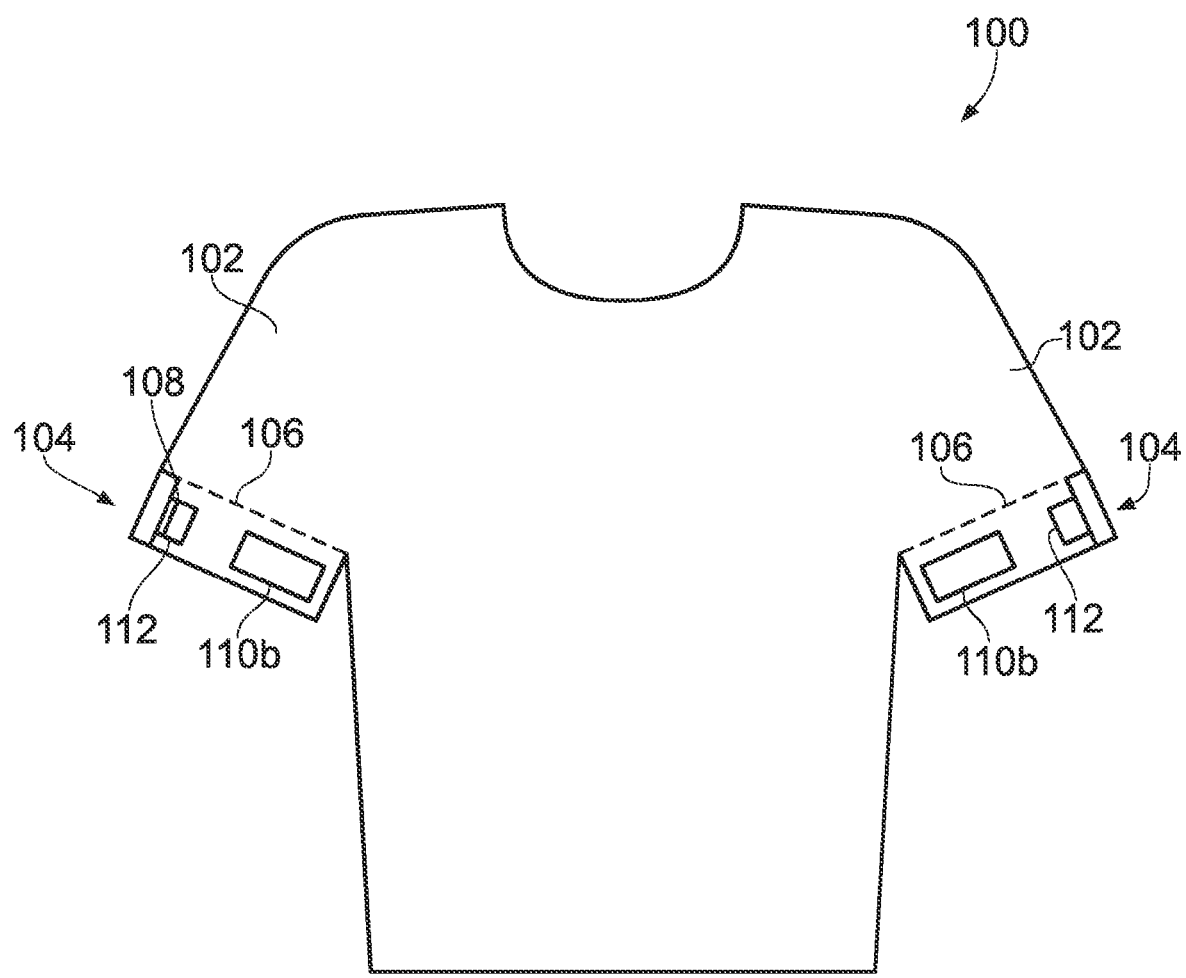
FIG. 1 is a sportswear garment comprising a compression member to adjustably compress at least one major vein according to a first embodiment.

FIG. 1 shows a t-shirt 100 having first and second sleeves 102 each including an integrated adjustable strap 104. The integrated adjustable strap 104 on the first sleeve and the second sleeve 102 may be substantially equivalent. The integrated adjustable strap 104 includes an elastic strap 108 in a housing 106. The elastic strap 108 may be made from twill tape or rubber. In FIG. 1, the elastic strap 108 is in a first neutral position wherein the elastic strap 108 is relaxed and is not compressing any major veins. The housing 106 is formed by folding an end of the sleeve 102 underneath itself and securing an edge of the end of the sleeve 102 to the inside of the sleeve 102, for example, by stitching or by gluing using a fabric adhesive. A width of the housing should be substantially, or slightly wider than, a width of the elastic strap 108. The width of the elastic strap 108 may be between 2 to 3 cm, preferably 2.5 cm. This width allows localised pressure to the desired area whilst being wide enough to distribute the pressure on a surface of an associated limb to reduce pain on said limb.

In an alternative example, the housing 106 may be formed by stitching a separate piece of fabric over the top of a fabric of the t-shirt 100. The housing 106 serves to obscure the elastic strap 108 such that the t-shirt 100 may resemble an unmodified sportswear t-shirt. In FIG. 1, only part of a second end of the elastic strap 108 is exposed. A first end, middle portion and a rest of the second end is within the housing 106. The exposed part of the second end serves as a tab 112 which can be easy to hold and grip for stretching the elastic strap 108. The tab 112 may be reinforced by having the second end of the elastic strap folded back on itself to double the thickness of the tab 112. The tab 112 may be reinforced by folding a strip of metal over an end of the tab. The strip of metal may be secured to the tab 112 by teeth on each end which penetrate the tab 112.

The first end is fixedly attached to an inside of the housing 106. The first end may be attached by looping the first end through a metal buckle 103 (see FIG. 9), wherein the metal buckle 103 (see FIG. 9) is attached to the inside of the housing 106, and stitching the first end back on itself over the metal buckle 103 (see FIG. 9). Alternatively, the first end may be fixedly attached by stitching the first end directly into the garment or by adhering using a fabric adhesive. The second end may be fed through the housing around the circumference of the user's upper bicep and also threaded through the metal buckle 103 (see FIG. 9). The double thickness tab 112 serves to prevent the second end of the elastic strap 108 receding too far into the housing 106.

A releasable connector 110, or a first part 110a (see FIG. 9) of a releasable connector 110, for detachably attaching the second end to the garment is fixedly attached to the second end. The garment 100 may comprise a second part 110b of the releasable connector for attaching the second end to the garment. The first 110a (see FIG. 9) and second 110b parts of the releasable connector 110 for detachably attaching the second end to the garment comprise a hook and loop type fastening 110, for example Velcro®. One of the loops or hooks 110b of the hook and loop type fastening 110 is positioned on an outside surface of the housing 106. Preferably, the loops of the hook and loop type fastening 110 are positioned on the outside surface of the housing 106 to avoid discomfort to the user who may contact the second 110b parts of the releasable connector 110 for detachably attaching the second end when wearing the t-shirt 100. Another of the hooks or loops 110a (see FIG. 9) of the hook and loop type fastening 110 is attached to the outside surface of the second end of the elastic strap 108. Thus, the second end can be detachably attached to the t-shirt sleeve 102 by engaging the hooks 110a (see FIG. 9) with the loops 110b of the hook and loop type fastening 110. The second end 112 may be detachable attached to the t-shirt sleeve 102 using other methods. For example, the second end may comprise: an eyelet, a button or a popper attached to the outside surface of the elastic strap 108 for engagement with a metal loop, button hole or popper, respectively, attached to the outside surface of the housing 106.

Figure 2:
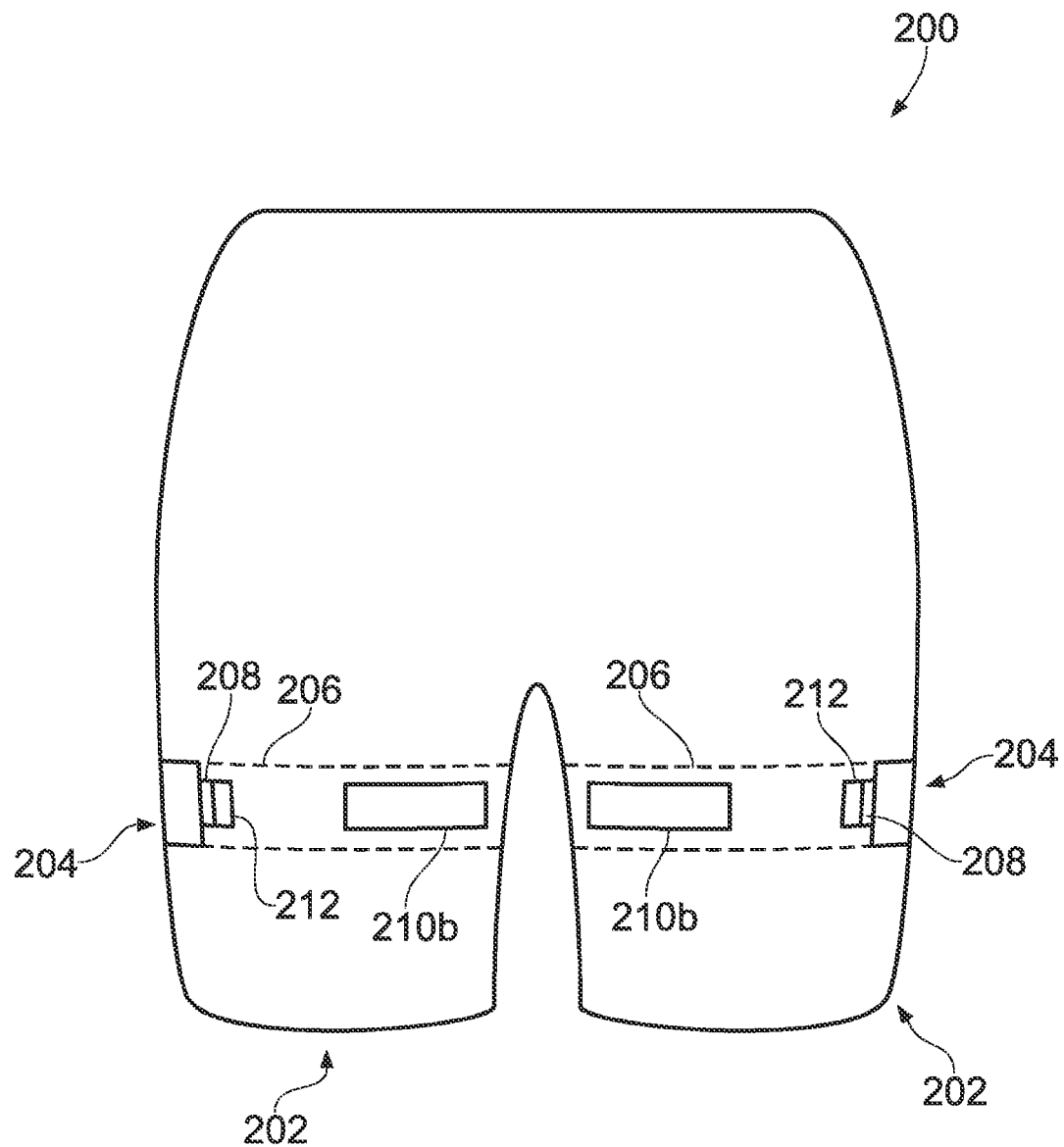
FIG. 2 a sportswear garment comprising a compression member to adjustably compress at least one major vein according to a second embodiment.

FIG. 2 shows a pair of shorts 200 comprising a first and a second leg 202 each including an integrated adjustable strap 204. The integrated adjustable strap 204 is substantially similar to the integrated adjustable strap 104 described in the t-shirt 100 of FIG. 1. The integrated adjustable strap 204 has an elastic strap 208 within a housing 206. A first end of the elastic strap 208 is attached within the housing 206 and an outside surface of a second end of the elastic strap 208 has a releasable connector 210, or a first part of a releasable connector 210a (see FIG. 9), for detachably attaching to the leg 202 of the pair of shorts 200. A second part 210b of the releasable connector 210 for detachably attaching the elastic strap 208 to the leg 202 may be attached to an outside surface of the housing 206.

Similarly to the arrangement as described in FIG. 1, a first end, middle portion and a part of a second end is within the housing 206. An exposed part of the second end serves as a tab 212 which can be easy to hold and grip for moving the elastic strap 208. The tab 212 may be reinforced by having the second end of the elastic strap folded back on itself to double the thickness of the tab 212.

The first end of the elastic strap 208 is fixedly attached to an inside of the housing 206. The first end may be attached by looping the first end through a metal buckle 203 (see FIG. 9), wherein the metal buckle 203 (see FIG. 9) is attached to the inside of the housing 206, and stitching the first end back on itself over the metal buckle 203 (see FIG. 9). Alternatively, the first end may be fixedly attached by stitching the second end directly into the garment or by adhering using a fabric adhesive. The second end may be fed through the housing 206 around a circumference of the user's upper thigh and also threaded through the metal buckle 203 (see FIG. 9). The double thickness tab 212 serves to prevent the second end of the elastic strap 208 receding too far into the housing 206.

In the example of FIG. 2, the releasable connector 210 for detachably attaching the second end of the elastic strap 208 to the leg 202 is a hook and loop type fastening 210. Preferably, the first part 210a (see FIG. 9) of the releasable connector for detachably attaching the elastic strap 208 to the leg 202 is the hooks of the hook and loop type fastening and the second part 210b of a hook and loop type fastening is the loops of the hook and loop type fastening. The integrated adjustable strap 204 is located just below the crotch of the pair of shorts such that the integrated adjustable strap 204 is over the upper part of the thigh muscle when the pair of shorts is being worn by a user. In the example of FIG. 2, the housing 206 is formed by stitching or gluing a piece of material over the pair of shorts 200. In an alternative embodiment, the housing 206 could be formed by folding an end of the leg 202 of the pair of shorts 200 underneath itself and securing an edge of the end of the leg 202 to the inside of the leg 202, for example, by stitching or by gluing using a fabric adhesive. A width of the end of the leg 202 to be folded under should be substantially, or slightly wider than, the width of the elastic strap 208. The width of the elastic strap 208 may be between 2 to 3 cm, preferably 2.5 cm. In this arrangement, the length of the leg 202 will be such that the end of the leg 202 comes down to the upper thigh. Thus, a housing made from this method leads to a pair of shorts of short leg length.

Figure 3:
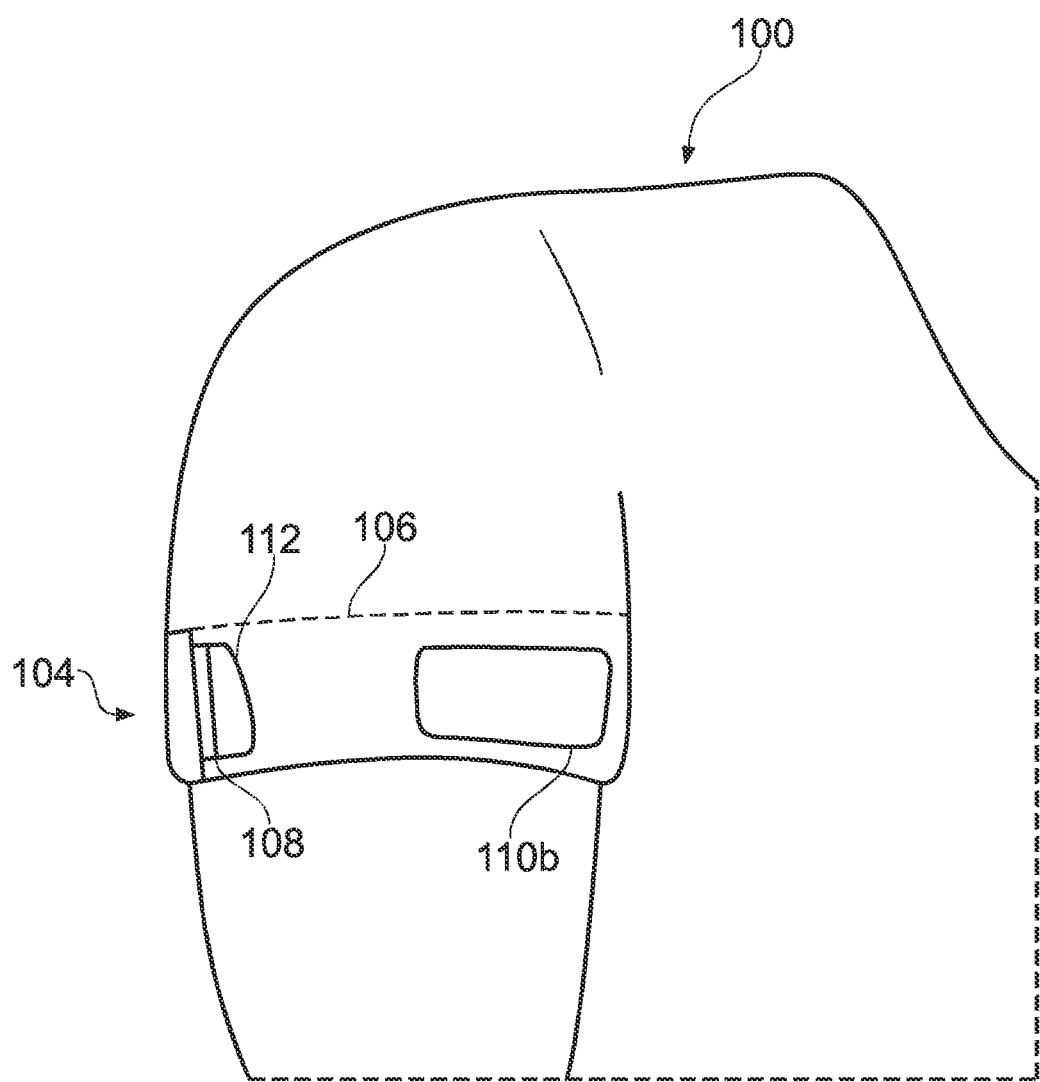
FIG. 3 is an enlarged view of the compression member in the garment of the first embodiment, wherein the compression member is in a first, neutral position.

FIG. 3 shows an enlarged view of the sleeve 102 of the t-shirt 100 including the integrated adjustable strap 104. FIG. 3 shows the integrated adjustable strap 104 in the first position wherein the elastic strap 108 is not under tension. The length of the elastic strap 108 may vary depending on the size of the t-shirt 100. A longer elastic strap 108 will be needed for a user with a larger bicep girth than a user with a smaller bicep girth. The integrated adjustable strap 104 is positioned over the upper part of the bicep proximate to a user's armpit when the t-shirt 100 is being worn by the user.

Figure 4:
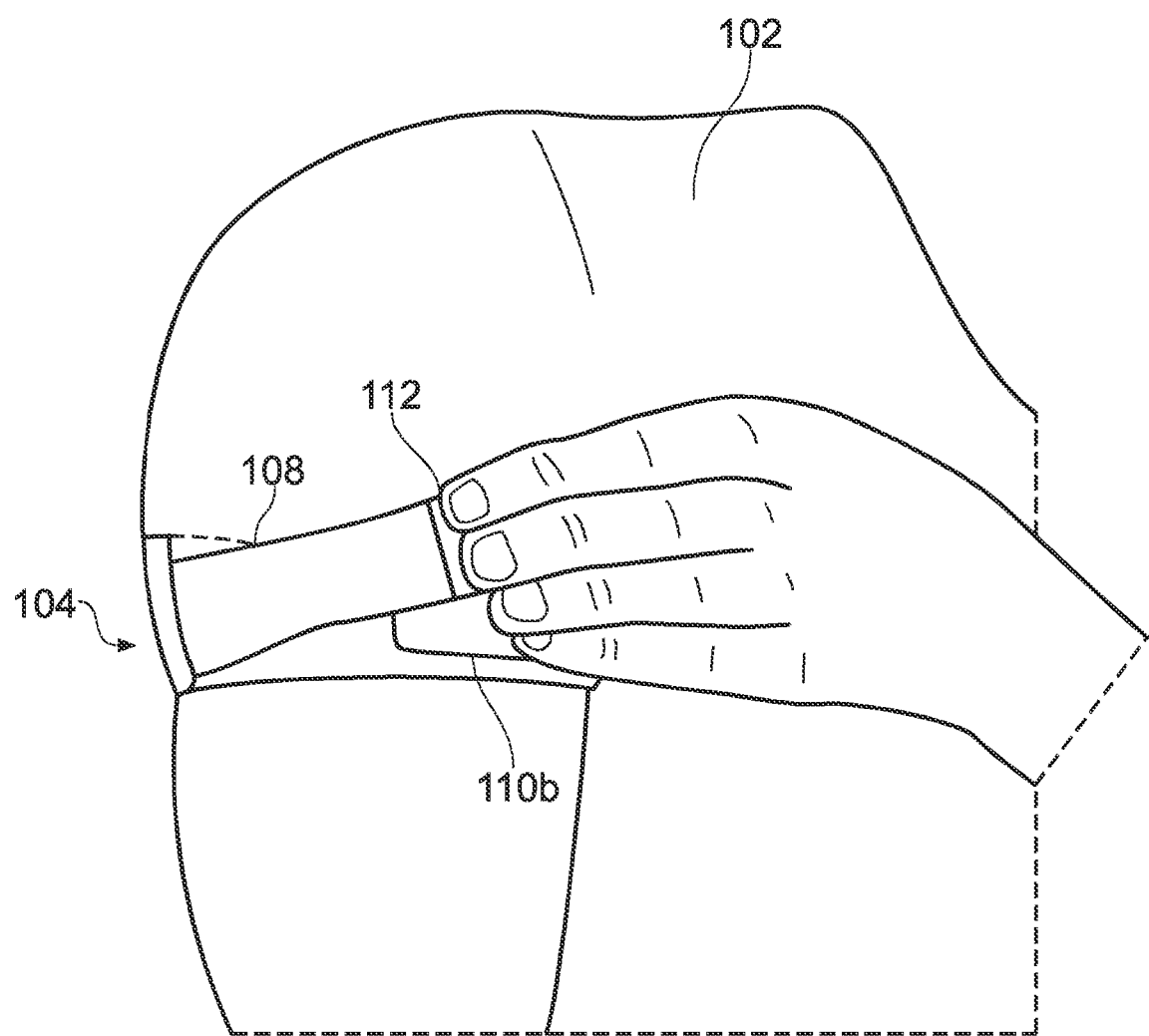
FIG. 4 is an enlarged view of the compression member in the garment of the first embodiment, wherein a user is adjusting the compression member from the first, neutral position to a second, engaged position.

FIG. 4 shows the user moving the elastic strap 108 from the first neutral position wherein the elastic strap 108 is relaxed to the second position wherein the elastic strap 108 is under tension. A length of the elastic strap 108 should be such that the elastic strap 108 must be stretched to engage the first part 110a (see FIG. 9) of the hook and loop type fastening 110 on the elastic strap 108 with the second part 110b of the hook and loop type fastening 110 on the housing 106. The user moves the elastic strap 108 from the first neutral position to the second position by pinching the tab 112 in their thumb and forefinger and pulling the tab 112 away from the fixedly attached first end of the elastic strap 108. The amount of tension in the elastic strap 108 can be adjusted by moving the second end of the elastic strap 108 further away from the attachment of the first end of the elastic strap 108.

Figure 5:
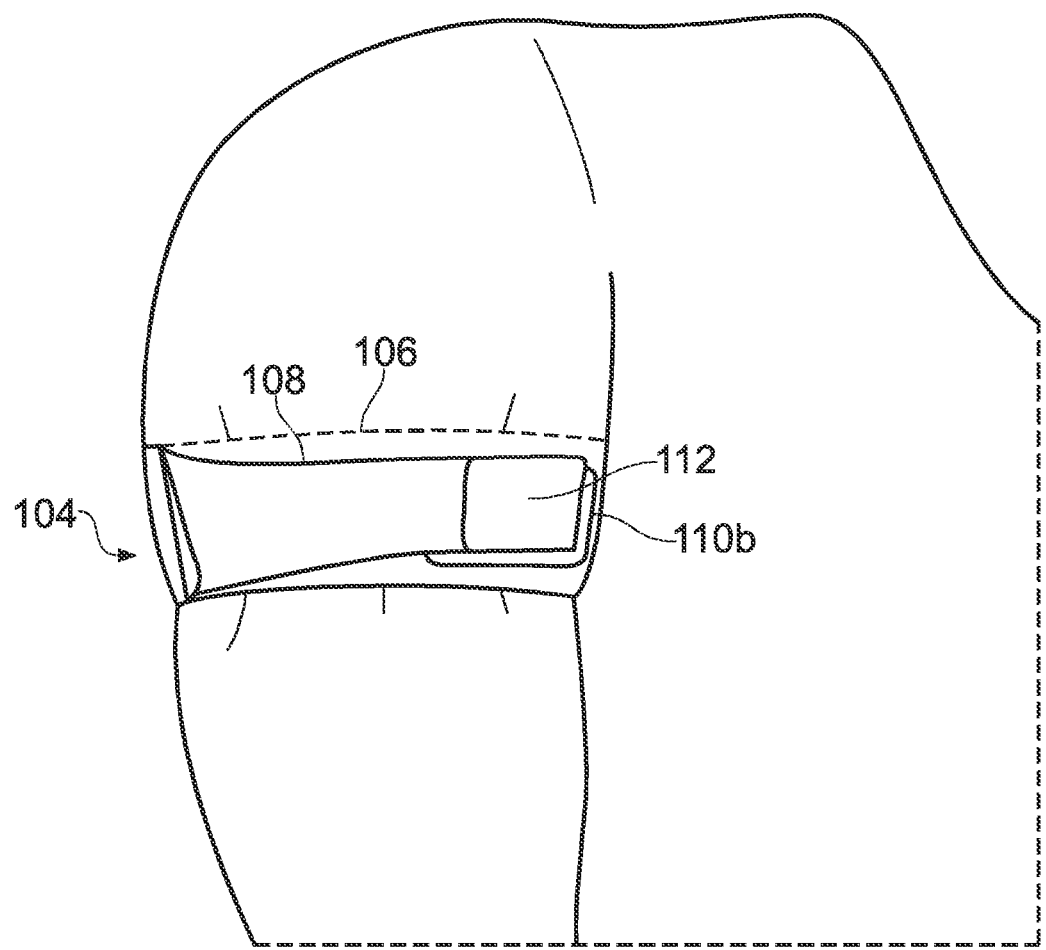
FIG. 5 is an enlarged view of the compression member in the garment of the first embodiment, wherein the compression member is in the second, engaged position.

FIG. 5 shows the t-shirt 100 wherein the second end of the elastic strap 108 is detachably attached. The first 110a (see FIG. 9) and second 110b parts of the hook and loop type fastening 110 engage to secures the elastic strap 108 in a state of tension. In FIG. 5, the elastic strap 108 is under tension such that the major vein, associated with the bicep that the strap is covering, is compressed to reduce blood flow through said major vein. Preferably, the blood flow is reduced to between 40 to 50%. The integrated adjustable strap 104 may have markers (not shown) along a length of the housing 106, the elastic strap 108 and/or the hook and loop type fastening 110 for displaying the amount of tension in the elastic strap 108. In this way, the user has a value associated with the amount of tension they have added to the elastic strap 108. This may provide the user with an easy way to return to the amount of tension added to the elastic strap 108 for subsequent BFR use of the sportswear garment 100.

Figure 6:
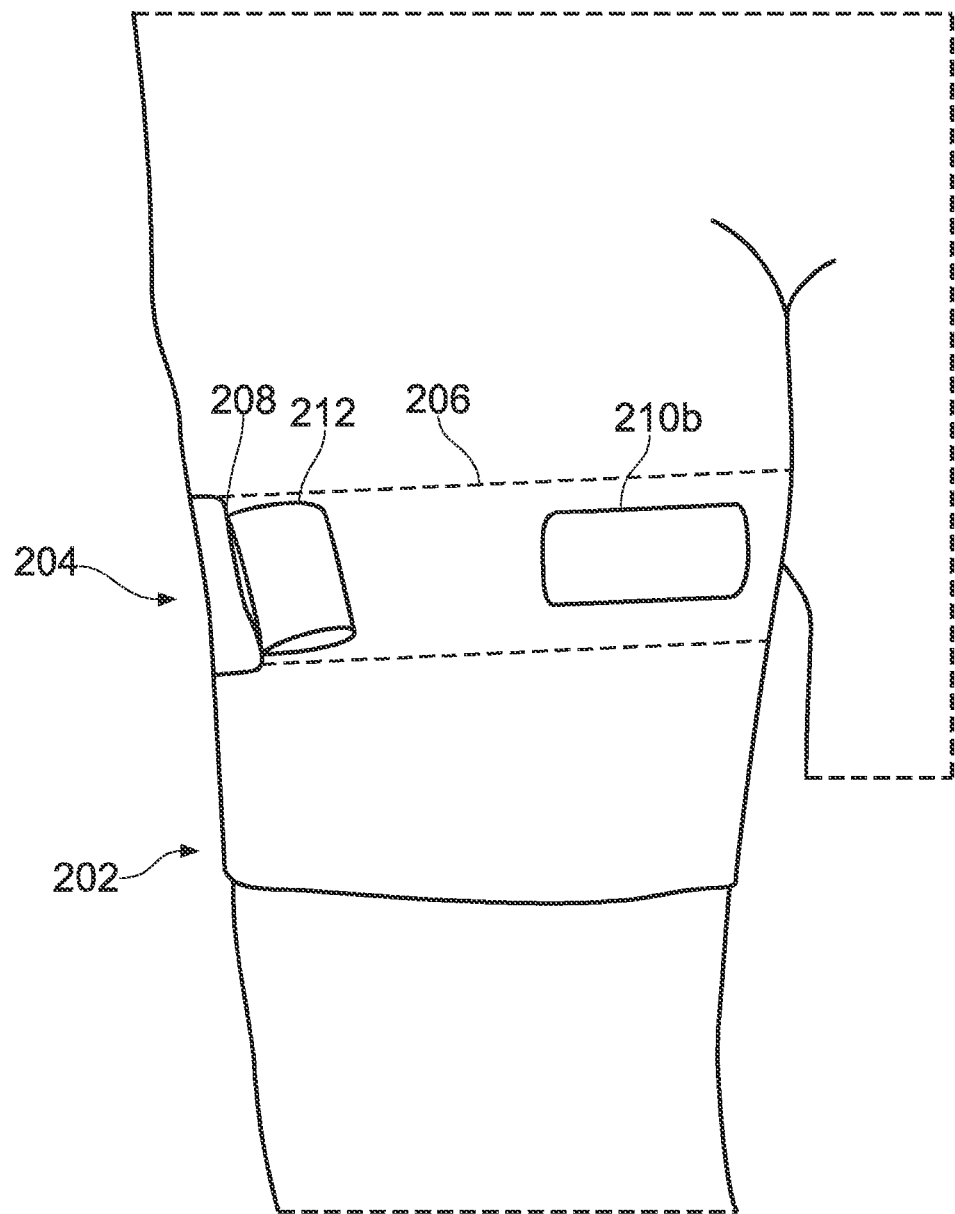
FIG. 6 is an enlarged view of the compression member in the garment of the second embodiment, wherein the compression member is in a first, neutral position.

FIG. 6 shows an enlarged view of the leg 202 of the pair of shorts 200 including the integrated adjustable strap 204. The elastic strap 208 in the first position wherein the elastic strap 208 is not under tension. The length of the elastic strap 208 may vary depending on the size of the pair of shorts. A longer elastic strap 208 will be needed for a user with a larger thigh girth than a user with a smaller thigh girth. The housing 206 and the integrated adjustable strap 204 are positioned over the upper part of the thigh proximate to a user's groin when the pair of shorts is being worn by the user.

Figure 7:
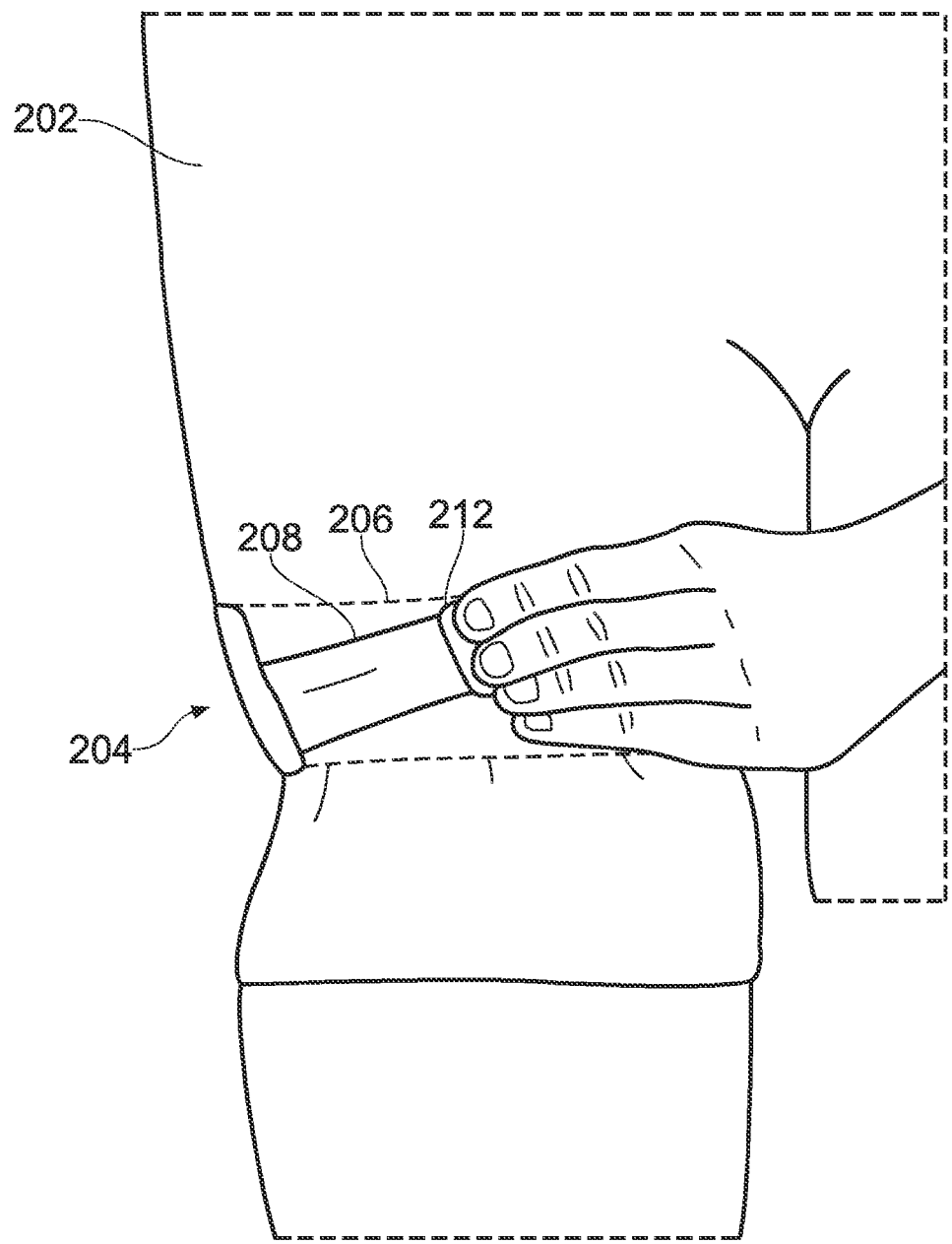
FIG. 7 is an enlarged view of the compression member in the garment of the second embodiment, wherein a user is adjusting the compression member from the first, neutral position to a second, engaged position.

FIG. 7 shows a user moving the elastic strap 208 from the first position, wherein the elastic strap 108 is relaxed, to the second position, wherein the elastic strap 208 is under tension. The user moves the elastic strap 208 from the first neutral position to the second position by pinching the tab 212 in their thumb and forefinger and pulling the tab 212 away from the fixedly attached first end of the elastic strap 208. Preferably, the compression on the major veins should be such that the blood flow is restricted between around 40-50% of the original flow. The amount of tension in the elastic strap 208 can be adjusted by moving the second end of the elastic strap 208 further away from the attachment of the first end of the elastic strap 208.

Figure 8:
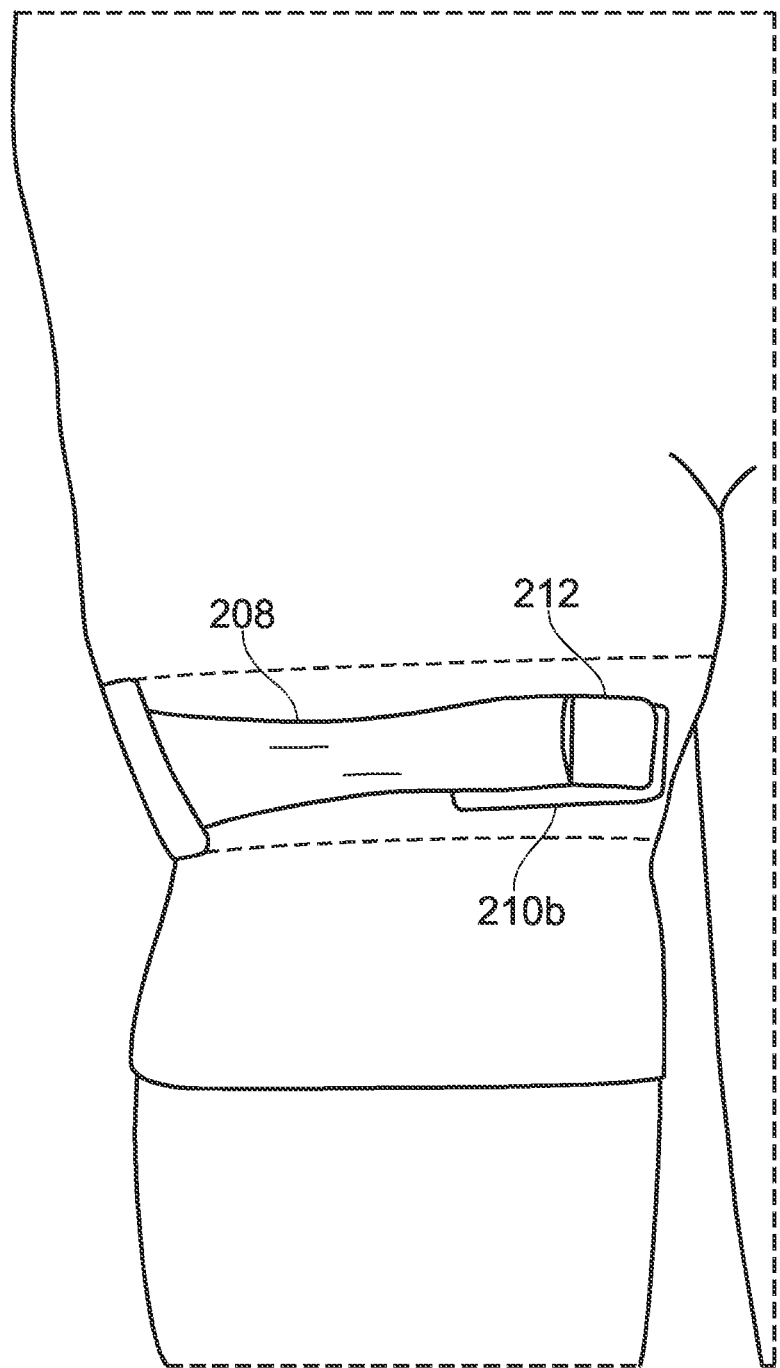
FIG. 8 is an enlarged view of the compression member in the garment of the second embodiment, wherein the compression member is in the second, engaged position.

FIG. 8 shows a user wearing the pair of shorts 200 wherein the second end of the elastic strap 208 is detachably attached. A length of the elastic strap 208 should be such that when the first part 210a (see FIG. 9) of the hook and loop type fastening 210 on the elastic strap 208 is engaged with the second part 210b of the hook and loop type fastening 210 on the housing, the elastic strap 208 is under tension. The elastic strap is secured in a state of tension by engagement of the hook and loop type fastening 210. The integrated adjustable strap 204 may have markers (not shown) along a length of the housing 206, the elastic strap 208 and/or the hook and loop type fastening 210 for displaying the amount of tension in the elastic strap 208. In this way, the user has a value associated with the amount of tension they have added to the elastic strap 208. This may provide the user with an easy way to return to the amount of tension added to the elastic strap 208 for subsequent BFR use of the sportswear garment 200.

Figure 9:
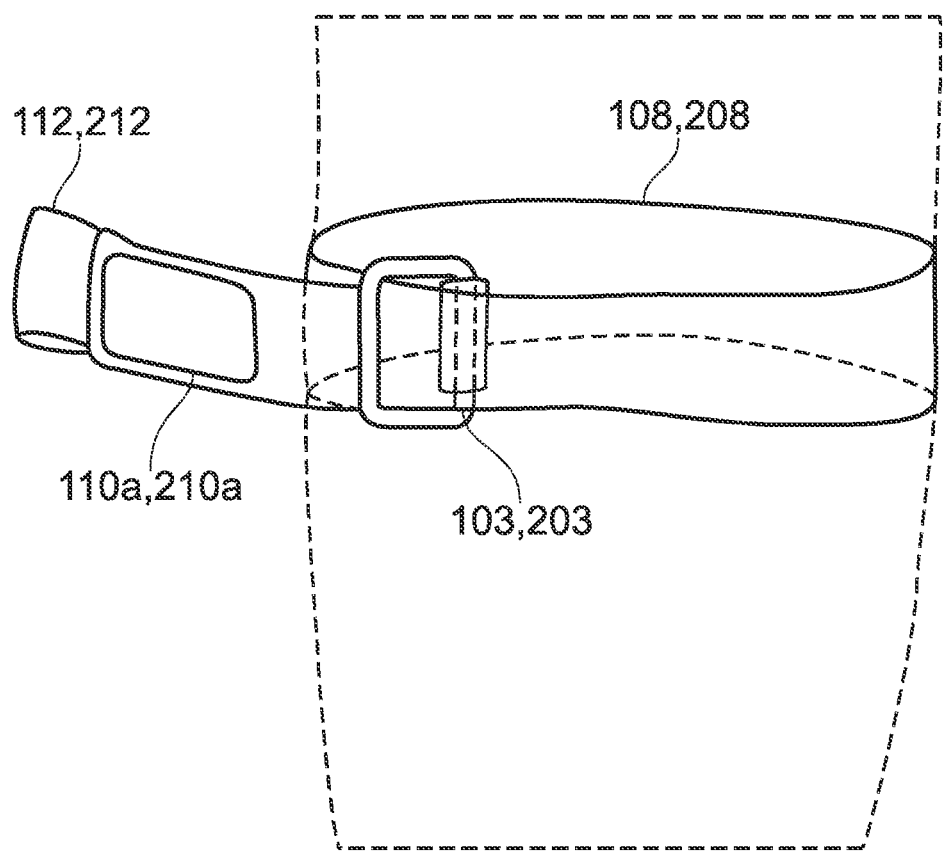
FIG. 9 shows the compression member without a housing.

FIG. 9 shows the integrated adjustable strap 104, 204 without the housing 106, 206 to more clearly demonstrate the arrangement of the elastic strap 108, 208. The metal buckle 103, 203 is attached to the housing. A first end of the elastic strap 108, 208 is attached to the metal buckle 103, 203. This may be achieved by stitching a fabric loop around a bar of the buckle. The elastic strap is wound round a circumference of the opening for a user's limb in the garment and thread through a second bar of the metal buckle 103, 203. Tab 112, 212 is thicker than an aperture between the bars of the metal buckle 103, 203 which may prevent the second end of the elastic strap 108, 208 receding too far into the housing 106, 206. The first part 110a, 210a of the releasable connector for attaching the second end to the garment is attached to the outside surface of the elastic strap such that when the elastic strap is folded back over the buckle, the first part 110a, 210a engages with the second part 110b, 210b on the outside of the housing 106, 206.

Figure 10:
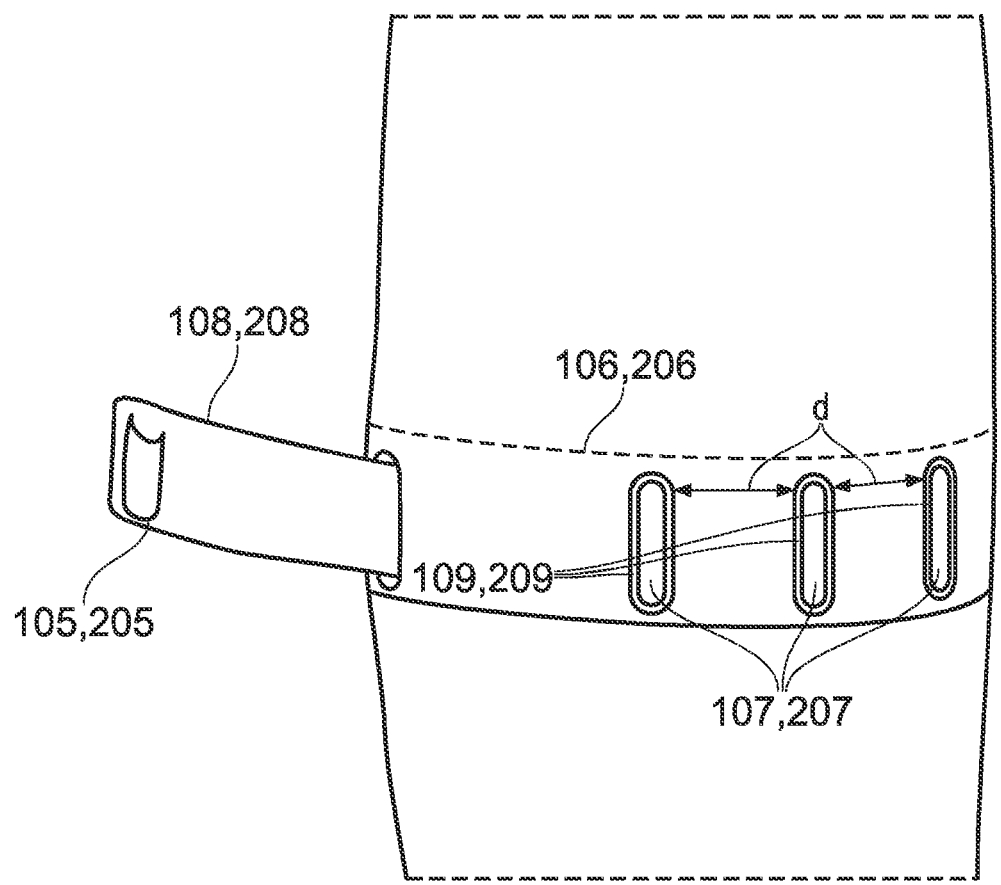
FIG. 10 shows an alternative arrangement of the compression member.

FIG. 10 shows an alternative arrangement for detachably attaching the second end of the elastic strap 108, 208 to the garment 100, 200. A catch 105, 205 is configured to be hooked though one of a plurality of eyelets 107, 207. The eyelets 107, 207 are positioned in the housing 106, 206 and are spaced apart by a distance d. The eyelets 107, 207 are reinforced to stop fraying of the housing 106, 206 material and to help support the force of the catch 105, 205 on the eyelet 107, 207. The length of the catch 105, 205 is substantially equal to the width of the elastic strap 108, 208. This enables the elastic force on the eyelet 107, 207 from the elastic strap 108, 208 provided by the catch 105, 205 to be distributed along the length of the catch 105, 205 to prevent damage to the housing 106, 206. A radius of the catch 105, 205 may be between 2 and 7 mm. This may ensure adequate attachment within the eyelet 107, 207 without causing discomfort to the user by the catch protruding into their skin. The catch 105, 205 may be made from a metal such as aluminium or steel. Preferably, the catch 105, 205 is made from an oxidation-resistant metal. This may ensure durability of the catch 105, 205 in the presence of sweat which is likely to be present from the user wearing the sportwear garment 100, 200. The eyelets 107, 207 may be reinforced by reinforcement elements 109, 209, for example, folding a thin piece of material around the eyelet 107, 207. Preferably this material is an oxidation-resistance metal. The single catch 105, 205 and plurality of eyelets 107, 207 may also have a better aesthetic than the loop and hook type fastening 110, 210. Furthermore, the single catch 105, 205 and/or the reinforcement elements 109, 209 may be embossed with a logo of the sportswear garment.

Instead of the markers for displaying the amount of tension in the elastic strap 108, 208, the reinforced eyelets 107, 207 themselves may serve to display the amount of tension in the elastic strap. For example, the user can remember that they had the catch 105, 205 hooked through the second eyelet 107, 207 of three potential eyelets 107, 207.

Figure 11:
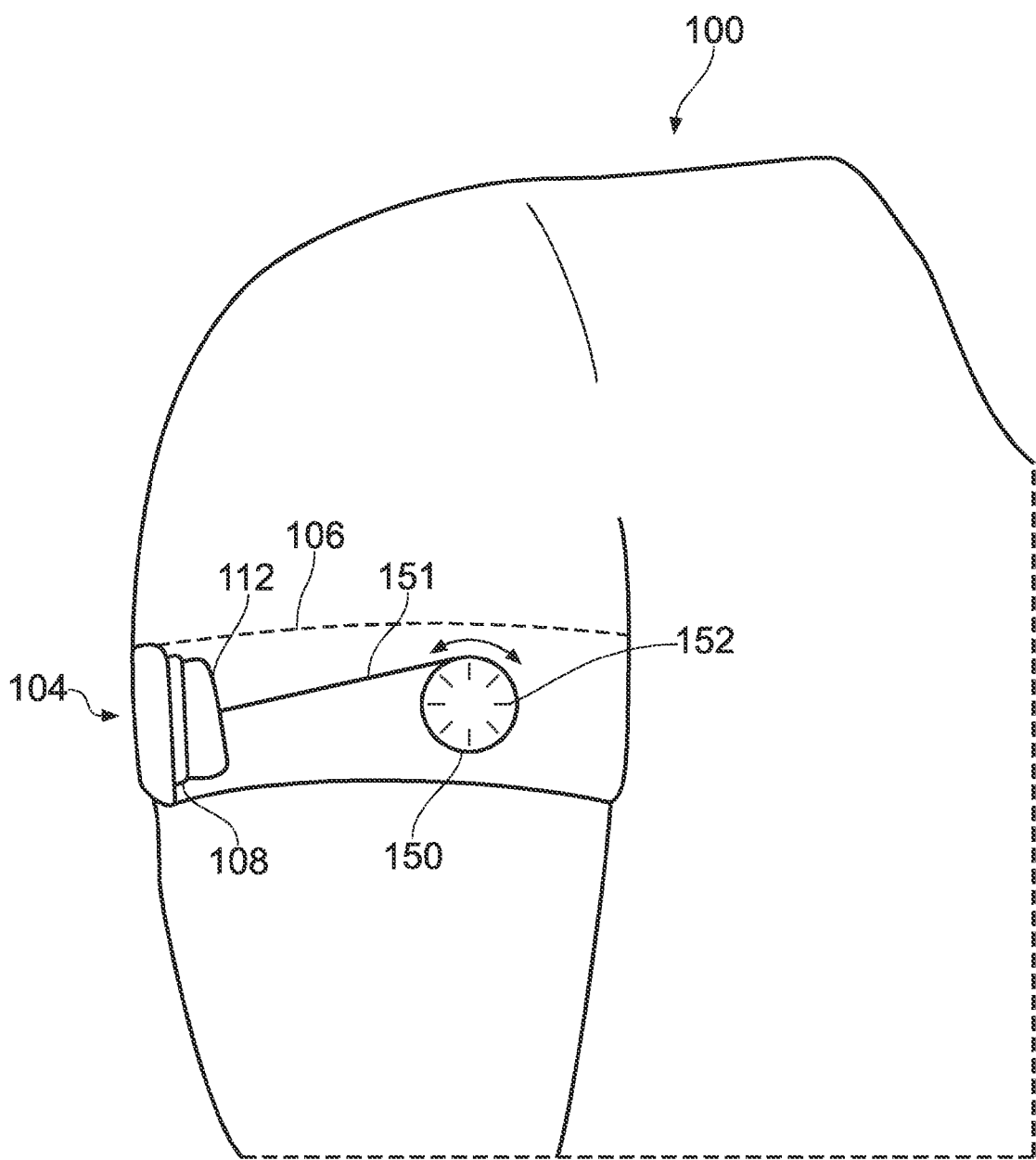
FIG. 11 shows a further alternative arrangement of the compression member.

FIG. 11 shows an enlarged view of the sleeve 102 of the t-shirt 100 including the integrated adjustable strap 104. FIG. 10 shows the integrated adjustable strap 104 in the first position wherein the elastic strap 108 is not under tension. The length of the elastic strap 108 may vary depending on the size of the t-shirt 100. A longer elastic strap 108 will be needed for a user with a larger bicep girth than a user with a smaller bicep girth. The integrated adjustable strap 104 is positioned over the upper part of the bicep proximate to a user's armpit when the t-shirt 100 is being worn by the user. The elastic strap 108 can be tensioned by rotating a ratcheted dial 150 in a clockwise direction so as to wind a tensioning cord 151 onto a spool (not shown) connected to the dial 150. The tensioning cord 151 is connected to the second end 112 of the elastic strap 108. After exercise, when the user wishes to stop BFR training, the dial 150 can be rotated anticlockwise so as to release the tension in the elastic strap 108. The dial 150 is provided with indicia 152 so as to provide the user with an indication of the amount of tension in the elastic strap 108, and hence the degree of compression of the at least one major vein.

Figure 12:
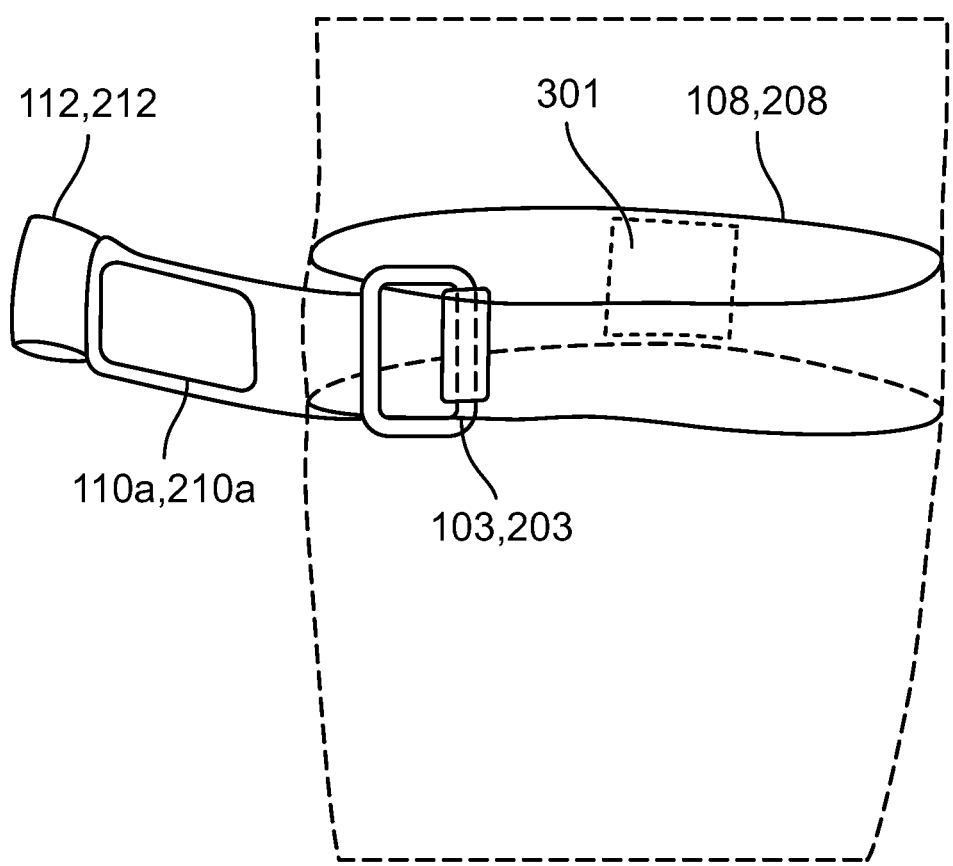
FIG. 12 shows an additional alternative arrangement of the compression member.

As seen in FIG. 12, in some embodiments, an underside of the elastic strap 108,208 may be provided with a pad or protrusion 301 configured to apply additional pressure on the user's limb at a position appropriate to restrict blood flow in at least one major vein but to allow blood flow in major arteries. The pad or protrusion 301 may be substantially solid, or may in some embodiments be cushioned for comfort. A position of the pad or protrusion 301 along the length of the elastic strap 108,208 may in some embodiments be adjustable by a user so as to allow correct positioning. The pad or protrusion 301 can be held in place with a clip or other securing device.

The garment described herein is not limited to a t-shirt or a pair of shorts as shown in the drawings. The garment may be any garment which has material covering a major muscle such as: a bicep, a thigh, a calf and a forearm, to name some non-limiting examples. The garment made be made from any suitable sportswear material such as: polyester, elastane or spandex, cotton and silk, to name a few non-limiting examples.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A blood flow restriction training garment comprising an integrated adjustable compression member to compress at least one major vein in a user's limb such that blood flow through the at least one major vein is restricted while permitting blood flow through major arteries in the user's limb; and
    a fabric housing in which the integrated adjustable compression member is at least partially contained so as to be obscured or hidden;
    wherein the integrated adjustable compression member comprises a strap, the strap having a first end, a middle portion, and a second end, wherein the first end of the strap is fixedly secured to an inside of the housing by stitching or by adhering and the second end of the strap is releasably secured to the garment by attaching the second end of the strap to an outside surface of the housing; and
    wherein either:
    i) the garment is a top or t-shirt and the integrated adjustable compression member is integrated with a sleeve of the top or t-shirt such that, in use, the integrated adjustable compression member is positioned over an upper part of the user's arm proximate to the user's armpit; or
    ii) the garment is a pair of shorts or a pair of trousers and the integrated adjustable compression member is integrated with a leg of the pair of shorts or pair of trousers such that, in use, the integrated adjustable compression member is positioned over an upper part of the user's thigh proximate to the user's groin.

2. The garment of claim 1, wherein the strap is an elastic strap configured to be adjustable between a first configuration in which the integrated adjustable compression member does not compress the at least one major vein and a second configuration in which the elastic strap is under tension and compresses the at least one major vein.

3. The garment of claim 2, wherein at least one of the first and second ends of the elastic strap is moveable relative to the other of the first and second ends so as to adjust the elastic strap between the first and second configurations.

4. The garment of claim 3, wherein at least one of the first and second ends is connected to a rotary dial with a ratchet mechanism, and wherein a rotation of the dial allows the elastic strap to be tensioned.

5. The garment of claim 3, wherein the second end of the elastic strap is releasably secured to the garment by a catch and eyelet fastening.

6. The garment of claim 3, wherein the second end of the elastic strap is releasably secured to the garment by a hook and loop fastening.

7. The garment of claim 2 wherein an underside of the elastic strap is provided with a pad or protrusion configured to apply additional pressure on the user's limb at a position appropriate to restrict blood flow in at least one major vein but to allow blood flow in major arteries.

8. The garment of claim 7, wherein the pad or protrusion is substantially solid.

9. The garment of claim 7, wherein the pad or protrusion is cushioned.

10. The garment of claim 7, wherein a position of the pad or protrusion along the length of the elastic strap is adjustable.

11. The garment of claim 1, further comprising indicia to indicate an amount of compression applied by the integrated adjustable compression member to the at least one major vein.

12. A blood flow restriction training garment comprising:
    an integrated adjustable compression member to compress at least one major vein in a user's limb such that blood flow through the at least one major vein is restricted while permitting blood flow through major arteries in the user's limb; and
    a fabric housing in which the integrated adjustable compression member is at least partially contained;
    wherein the integrated adjustable compression member comprises a strap configured to be adjustable between a first configuration in which the integrated adjustable compression member does not compress the at least one major vein and a second configuration in which the strap is under tension and compresses the at least one major vein;
    wherein the strap has a first end, a middle portion, and a second end, and the first end of the strap is fixedly attached to an inside of the housing by stitching or by adhering and the first end and middle portion of the strap are within the housing;
    wherein the strap is an elastic strap, wherein at least one of the first and second ends is moveable relative to the other of the first and second ends so as to adjust the elastic strap between the first and second configurations, and wherein the second end of the elastic strap at least partially protrudes from the housing when the elastic strap is in the first configuration;
    wherein the second end of the elastic strap is releasably secured to the garment by a hook and loop fastening, and wherein one part of the hook and loop fastening is disposed on an exterior surface of the housing and a complementary part of the hook and loop fastening is disposed at or proximate to the second end of the elastic strap
    and wherein either:
    i) the garment is a top or t-shirt and the integrated adjustable compression member is located in a sleeve of the top or t-shirt such that, in use, the integrated adjustable compression member is positioned over an upper part of the user's arm proximate to the user's armpit; or
    ii) the garment is a pair of shorts or a pair of trousers and the integrated adjustable compression member is located in a leg of the pair of shorts or pair of trousers such that, in use, the integrated adjustable compression member is positioned over an upper part of the user's thigh proximate to the user's groin.

13. The garment of claim 12, wherein the first end of the elastic strap is fixedly secured to the garment and the second end of the elastic strap is configured to be releasably secured to the garment.

14. The garment of claim 12, further comprising indicia to indicate an amount of compression applied by the integrated adjustable compression member to the at least one major vein.

15. The garment of claim 14 wherein an underside of the elastic strap is provided with a pad or protrusion configured to apply additional pressure on the user's limb at a position appropriate to restrict blood flow in at least one major vein but to allow blood flow in major arteries.

16. A blood flow restriction training garment comprising:
   an integrated adjustable compression member to compress at least one major vein in a user's limb such that blood flow through the at least one major vein is restricted while permitting blood flow through major arteries in the user's limb; and
   a fabric housing in which the integrated adjustable compression member is at least partially contained, the housing comprising an inside and an outside surface;
   wherein the integrated adjustable compression member comprises an elastic strap configured to be adjustable between a first configuration in which the integrated adjustable compression member does not compress the at least one major vein and a second configuration in which the elastic strap is under tension and compresses the at least one major vein;
   wherein the elastic strap has a first end, a middle portion, and a second end;
   wherein the first end of the elastic strap is fixedly attached to the inside of the housing by stitching or by adhering;
   wherein the first end and middle portion of the strap are within the housing;
   wherein the second end of the elastic strap is releasably secured to the garment by a hook and loop fastening, the hook and loop fastening comprising hooks and loops;
   wherein the loops of the hook and loop fastening are positioned on the outside surface of the housing and the hooks of the hook and loop fastening are positioned on the second end of the elastic strap;
   and wherein either:
   i) the garment is a top or t-shirt and the integrated adjustable compression member is located in a sleeve of the top or t-shirt such that, in use, the integrated adjustable compression member is positioned over an upper part of the user's arm proximate to the user's armpit; or
   ii) the garment is a pair of shorts or a pair of trousers and the integrated adjustable compression member is located in a leg of the pair of shorts or pair of trousers such that, in use, the integrated adjustable compression member is positioned over an upper part of the user's thigh proximate to the user's groin.

17. The garment of claim 16, further comprising indicia to indicate an amount of compression applied by the integrated adjustable compression member to the at least one major vein.

* * * * *